United States Patent [19]

Greenberg

[11] Patent Number: 5,443,063
[45] Date of Patent: Aug. 22, 1995

[54] CUFFED ORO-PHARYNGEAL AIRWAY

[75] Inventor: Robert S. Greenberg, Baltimore, Md.

[73] Assignee: The Johns Hopkins University, Baltimore, Md.

[21] Appl. No.: 114,353

[22] Filed: Aug. 31, 1993

[51] Int. Cl.$^6$ ............................................. A61M 16/04
[52] U.S. Cl. ............................ 128/207.15; 128/207.14; 128/200.26; 604/275
[58] Field of Search ....................... 128/200.26, 207.14, 128/207.15, 202.28, 203.11; 604/275, 282

[56] References Cited

U.S. PATENT DOCUMENTS

| | | | |
|---|---|---|---|
| 1,567,500 | 12/1925 | Hein | 128/207.15 |
| 2,099,127 | 11/1937 | Leech | 128/207.15 |
| 3,543,751 | 12/1970 | Sheffer | 128/207.15 |
| 3,659,612 | 5/1972 | Shiley | 128/207.15 |
| 3,693,624 | 9/1972 | Shiley | 128/207.15 |
| 4,009,720 | 3/1977 | Crandall | 128/207.15 |
| 4,112,936 | 9/1978 | Blachy | 128/207.14 |
| 4,230,108 | 10/1980 | Young | 128/207.15 |
| 4,231,365 | 11/1980 | Scarberry | 128/207.15 |
| 4,327,720 | 5/1982 | Bronson | 128/207.15 |
| 4,351,330 | 9/1982 | Scarberry | 128/207.15 |
| 4,509,514 | 4/1985 | Brain | 128/207.15 |
| 4,688,568 | 8/1987 | Frass et al. | 128/207.15 |

FOREIGN PATENT DOCUMENTS 2225955  6/1990  United Kingdom .

OTHER PUBLICATIONS

R. S. Greenberg, M.D. and T. Toung, M.D.—The Cuffed Oro-Pharyngeal Airway—A Pilot Study—Anesthesiology—vol. 77, No. 3A, Sep., 1992, p. A558.
Boheimer et al, "A Self-Retaining Nasopharyngeal Airway", Anaesthesiology, vol. 45, Jan. 1990, pp. 72-73.
Joshi et al, "The Supraglottic Oropharyngeal Airway", Anaesthesiology, vol. 46, Feb. 1991, p. 151.
Feldman et al, "The Cuffed Pharyngeal Airay", Europeon Journal of Anaesthesiology, vol. 8, Feb. 1991, pp. 291-295.
John Pennant et al, "The Laryngeal Mask Airway", Anesthesiology, vol. 79, No. 1, Jul. 1993, pp. 144-163.
Shipway, "Airway for Intranasal Operations", The British Medical Journal, 1935, p. 767.
Dr. Mehta, "A Supraglottic Oropharyngeal Airway", Anaesthesia, vol. 45; 1990; pp. 893-894.
Boheimer, "A Self-retaining Nasopharyngeal Airway", Anaesthesia, vol. 45; 1990; pp. 72-73.
Josh et al "The Supraglottic Oropharyngeal Airway", Anaesthesia, vol. 46; 1991; p. 151.

Primary Examiner—Edgar S. Burr
Assistant Examiner—William J. Deane, Jr.
Attorney, Agent, or Firm—Cushman, Darby & Cushman

[57] ABSTRACT

A new type of airway, the cuffed oro-pharyngeal airway (COPA), is described, which may be used as a less cumbersome alternative to face mask/oral airway technique for maintenance of general anesthesia. The airway includes an elongated tube having a length such that the proximal end is adapted to be disposed adjacent to but outside the oral cavity of the patient and the distal end is adapted to be disposed in the lower pharynx of the patient, above the epiglottis. An inelastic, inflatable cuff is mounted to the tube adjacent the distal end. On inflation, the inflatable cuff displaces the soft palate against the nasopharynx to seal-off the nasal passages and defines a seal between the tube and the pharyngeal wall. The inflatable cuff also displaces the base of the patient's tongue, thereby locking the tube in the pharynx and displacing the patient's epiglottis to a more open disposition for more effective anesthesia gas delivery to the lungs.

20 Claims, 2 Drawing Sheets

CUFFED ORO-PHARYNGEAL AIRWAY

BACKGROUND OF THE INVENTION

1. Field of the Invention

The present invention relates to the establishment and maintenance of an airway, particularly during administration of anesthesia.

2. Description of the Related Art

The administration of anesthesia via face mask/oral airway technique requires continuous hands-on management in many cases, and can be quite cumbersome in various situations. Indeed, for example, it is difficult to administer intravenous medications while attempting to maintain an airway with this technique. Likewise, it is cumbersome to attempt to perform face mask anesthesia during ophthalmologic examination, ear examinations or similar procedures. This is because the mask, the anesthesiologist's hands, and the surgeon's hands are all in too small an area. Also, because of awkward hand positioning, a patent airway cannot be reasonably assured without repeated manipulation. This is both dangerous to the patient and interrupting to the surgeon. Radiation therapy is another situation where an anesthesiologist needs to maintain a patent airway yet must be distant from the patient, and may be reluctant to instrument the trachea repeatedly.

Solutions to this problem have taken form of (i) use of general anesthesia with endotracheal intubation, (ii) use of intravenous techniques without securing the airway with adjunctive devices, and (iii) use of the laryngeal mask. Endotracheal intubation will subject the patient to the risks of this procedure, including laryngoscopy, tracheal irritation, the need for deeper anesthetic, and the possible use of neuromuscular blocking agents. Intravenous techniques alone do not address the issue of a patent airway any more effectively. The laryngeal mask airway has gained some acceptance as a solution to these problems; however, it does require some technical facility, and at times, adjunctive equipment for application and is not itself without complications.

SUMMARY OF THE INVENTION

To offer a reasonable alternative solution for anesthesiologists, it is an object of this invention to minimize the amount of equipment around the face of the patient (mask, anesthesiologist's hands) during the surgical procedure.

It is a further object of the invention to provide a device which does not require the anesthesiologist to deviate from recognized and accepted safety standards, and which would be easily recognizable as an anesthesia device and therefore more readily acceptable to anesthesia personnel.

It is yet a further object of the invention to provide a device which is simple to apply, does not require extensive training or instruction to use and requires no special or additional equipment.

It is another object of the invention to provide a device which avoids manipulation of the larynx and subglottic structures, and thus avoids increased stimulation and avoids medical complications associated with devices which may impinge on or cause damage to the delicate laryngeal and supra-laryngeal structures. The device of the invention is thus sized so as to terminate above or proximal of the path of travel of the epiglottis.

Yet another object of the invention is to allow for a smooth transition through routine anesthetic care during induction and emergence.

Another object of the invention is to provide an airway device which when in place effectively seals the pharynx so that gas flow is confined to pass through the airway during spontaneous breathing yet will allow gas to escape if increased airway pressure is encountered.

Yet another object of the invention is to provide an airway with an inflatable cuff which displaces the base of the tongue so as to elevate the epiglottis to permit the free flow of gas to the lungs, thereby minimizing the risk of gas passing to the stomach and maximizing the effective delivery of anesthetic gases to the lungs with a reduced work of breathing.

It is still a further object of the invention to provide a structure that defines a seat for the tongue.

It is also an object of the invention to provide a device which can be produced simply and inexpensively and with minimal risk of biomedical response of the patient.

A unique airway called the cuffed oro-pharyngeal airway (COPA) is provided, in accordance with the present invention, to achieve the foregoing objects. More particularly, the foregoing objects of the invention are realized by providing an elongated tube having a length such that it extends from adjacent to but outside of the patient's oral cavity into the lower pharynx of the patient, above the epiglottis. A relatively inelastic, inflatable cuff is mounted to the tube adjacent its distal end. On inflation, the posterior portion of the cuff displaces the soft palate into engagement with the nasopharynx to seal-off the nasal passages. Further, the more distal portions of the cuff define a seal circumferentially around the tube between the tube and the pharyngeal wall. Finally, the anterior portion of the cuff displaces the base of the patient's tongue, thereby locking the tube in the pharynx and additionally displacing the patient's epiglottis to an elevated and open disposition for more effective anesthetic gas delivery to the lungs.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

DETAILED DESCRIPTION OF THE PRESENTLY PREFERRED EXEMPLARY EMBODIMENTS

Figure 1:
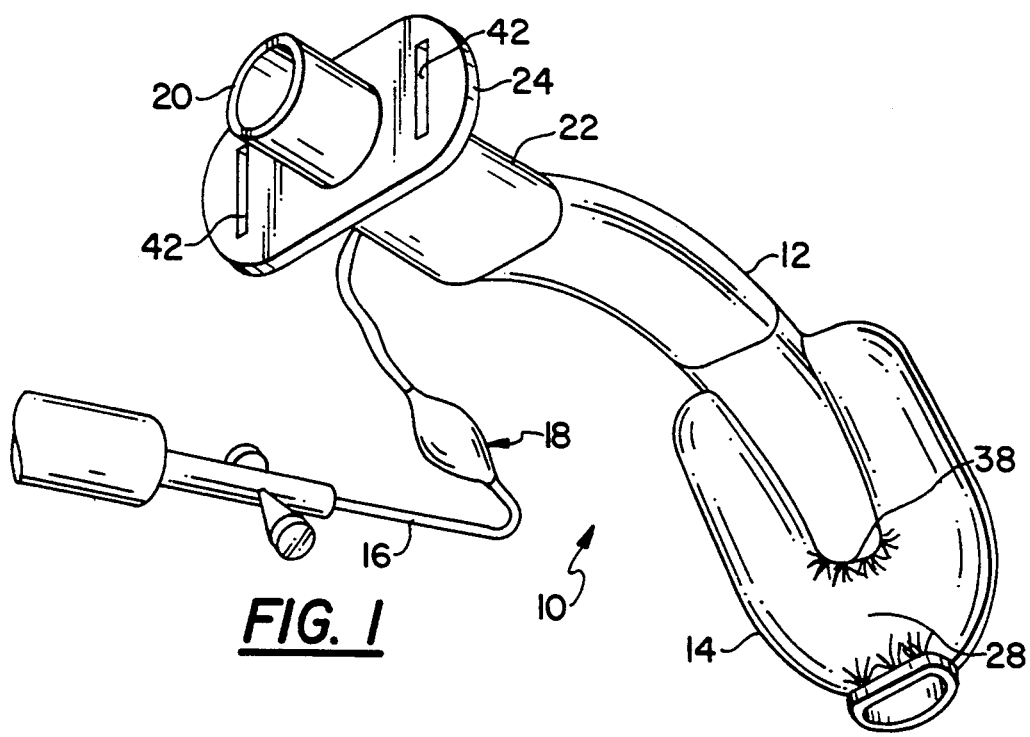
FIG. 1 is a perspective view of a cuffed oro-pharyngeal airway in accordance with an embodiment of the invention.
Figure 2:
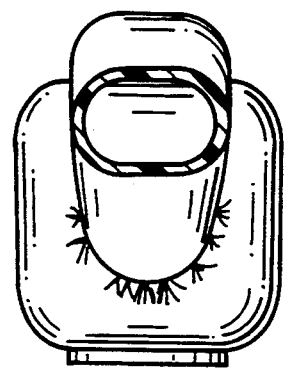
FIG. 2 is an inner plan view of the cuff of the device of FIG. 1.

In accordance with the invention, a Geudel-type oral airway or a preferably similarly-shaped cannula or tubular element 12 may be used as the base structure. An inflatable component 14 is provided on the distal portion of the airway 12. The inflatable component 14 may be defined by a membrane that is sealed at both proximal and distal aspects thereof to the airway to define, with the outer surface of the airway, a compartment for selectively receiving a fluid to inflate the same. In the alternative, the inflatable component 14 may be defined by a membrane that is configured to define an inflatable compartment, e.g. a inner tube-like membrane, that is placed over the tip of the airway and secured at both proximal and distal aspects thereof to the airway 12. The former type of structure is commonly referred to as a balloon whereas the latter type of structure is commonly referred to as a cuff. However, cuff will be used herein below to generically refer to the inflatable component, irrespective of how it is defined. A pilot tubing 16 with pressure balloon and check valve 18 is connected to the sealed cuff 14.

At the proximal end of the airway 12, a connector 20 of, for example, 15 mm outer diameter, is attached to sit over the core of the airway or otherwise formed as an extension to the base structure. The connector 20 is adapted to couple the airway directly or in sequence to an anesthesia circuit. As noted above, the connector may be provided as an integral part of the airway. In that event, any difference in cross-sectional shape between the proximal portion of the airway, which is disposed within the patient's oral cavity and is preferably of a shape designed for patient comfort, and the shape required to couple to the anesthesia maintenance circuit (generally circular) is accomplished by an abrupt or gradual cross-sectional shape transition, preferably in the area of the lip guard. Where the device is formed by interconnecting component parts, all seals and joints are secured with medical adhesive or may, depending on the material and configuration, be ultrasonically welded or secured in any other fashion deemed suitable or appropriate. Airways are preferably constructed to conform to sizes for neonates through large adults.

The first, most proximal segment of the airway extends axially so that when the airway is placed in a patient the proximal segment extends from outside the patient's teeth generally straight into the mouth. A bite block 22 and/or tooth/lip guard 24 is preferably provided on this segment of the airway, adjacent the proximal end. The bite block 22, if provided, is generally more rigid than the tubing 12 and prevents the tube from collapsing if the patient's teeth are clenched. The tooth/lip guard 24 limits the displacement of the device into the mouth and serves as an attachment point for stabilizing straps and the like, as described more particularly below. The lip guard can be oriented substantially perpendicular to the axis of the proximal most segment (FIG. 1). In the alternative, the lip guard can be oriented so that it is inclined relative to the central axis of the proximal segment (FIG. 3), consistent with the orientation of the airway tube in the oral cavity or as otherwise deemed necessary or desirable.

Figure 3:
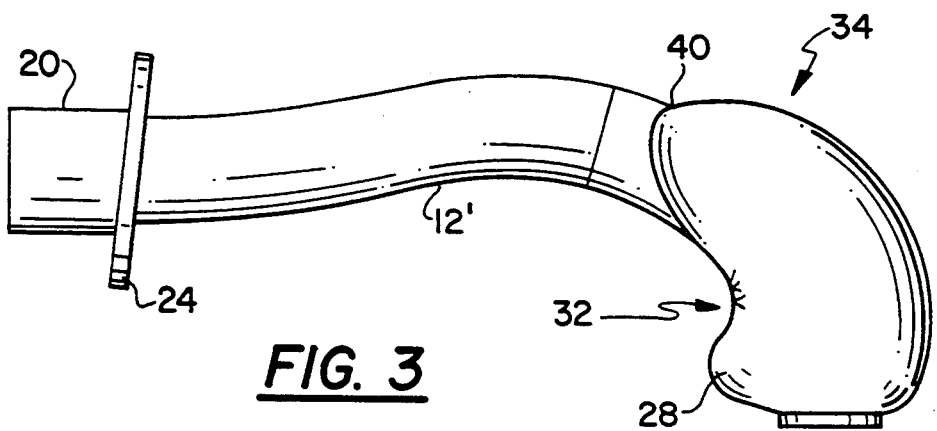
FIG. 3 is an elevational view of another cuffed oro-pharyngeal airway in accordance with the invention, showing modifications which may be made to the basic structure of FIG. 1.

The intermediate segment of the airway arches upwardly from the proximal segment so as to extend over the tongue whereas the distal segment of the airway depends downwardly from the intermediate segment, to direct air flow toward and from the trachea. The curvature at the tubing allows the tip of the distal end to rest above the tip of the epiglottis 26 in its open position. While in accordance with the invention the main tubing or base structure of the airway may thus be a Geudel-type airway, in accordance with another embodiment of the invention a lesser curvature is provided for the intermediate segment of the airway 12' and a more gradual transition is provided between the straight proximal segment and the intermediate, upwardly curved segment (FIG. 3). A smoother, continuously curved transition at that junction may increase patient comfort and facilitate the passage of instruments such as fiberoptics through the airway 12'.

The core airway 12, 12' is preferably semi-rigid. Thus, the core is preferably formed from a plastic that is flexible, but rigid enough not to collapse or kink when manually flexed.

The cuff 14 provided in accordance with the present invention is boat or shoe shaped to create a ventral/anterior projecting portion or protuberance 28 which is relatively short. As will become more apparent below, the effect of this portion of the cuff is to anteriorly displace the base of the tongue 30 and to allow for the residual bulk of the tongue to rest in the seat or pocket 32 created by the projecting portion. As explained below, the seat or pocket is provided by limited inflation, attachment to the core airway, or omission of the more proximal ventral aspect of the cuff and is bounded on the sides by the lateral aspects of the cuff which themselves contribute, in particular, to the sealing function of the cuff. The cuff is relatively smooth on the posterior side of the device but has some over-distension (either apparently or real) in the area 34. This will support the device in the patient's oral cavity, tend to position the core of the device in the mid-axis of the pharynx, and seal off the soft palate/nasopharynx (FIG. 5), as described more fully below.

The shape of the cuff of the invention may be accomplished in a variety of ways, as noted above. For example, the cuff may be formed so as to have differing thicknesses thereby controlling the shape achieved on inflation. Alternatively, the unique configuration of the cuff may be provided by a partially collapsed cuff attachment. A partial cuff attachment can be achieved by using a suitable medical adhesive or ultrasonic welding or by physically clamping down a portion of the cuff. As yet a further alternative, the cuff may itself be configured and attached to the airway so as to create the shoe-like shape of the cuff on inflation. The cuff is preferably a collapsible structure which is essentially non-distortable as opposed to a material, such as latex, which stretches. The cuff may then be held close to the airway before deployment by generating a negative pressure within the cuff to collapse it against the wall of the core airway.

The cuff is preferably smooth and continuously curved on all sides upon inflation and is sized and mounted so that when attached as shown, the cuff will not be able to overinflate past the distal tip 36 of the core airway 12. In that regard, a high radius/length ratio will leave a lot of material to flop over the distal tip 36. The attachment at 38 as well as at 40 will restrict the movement of this extra cuff. The addition of ribs or discrete nubs, extending circumferentially, diagonally and/or vertically, especially at 28 and 34 may be moderately helpful for traction and can be provided.

Figure 4:
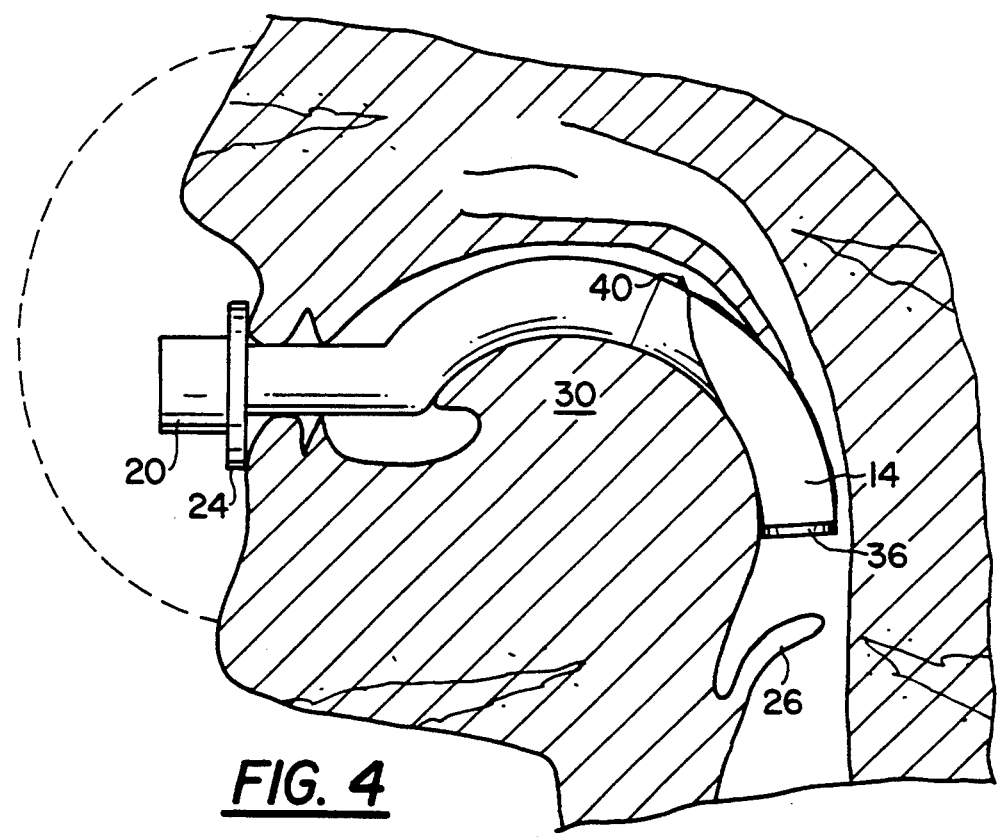
FIG. 4 is an elevational view showing a cuffed oro-pharyngeal airway in accordance with the invention disposed within a patient's oral cavity and with the cuff deflated.

As shown in FIG. 4, with the cuff deflated, the COPA resembles an ordinary oral airway. With the cuff inflated (FIG. 5), it establishes a high volume, low pressure seal at the level of the base of the tongue, soft palate, lateral pharyngeal wall, and posterior pharyngeal wall. This allows direct connection of the anesthetic circuit and maintenance of a seal from the patient's lungs to the anesthesia machine. As is apparent, the oral airway of the invention fills the upper airway and provides a breathing tube so that hands-off anesthesia administration is possible. The lip guard 24 may have ears with apertures 42 and/or hooks for strap attachment so that the airway may be secured at its proximal end with respect to the patient, with the strap(s) extending in a manner to secure the airway in position, as in around the patient's neck.

Figure 5:
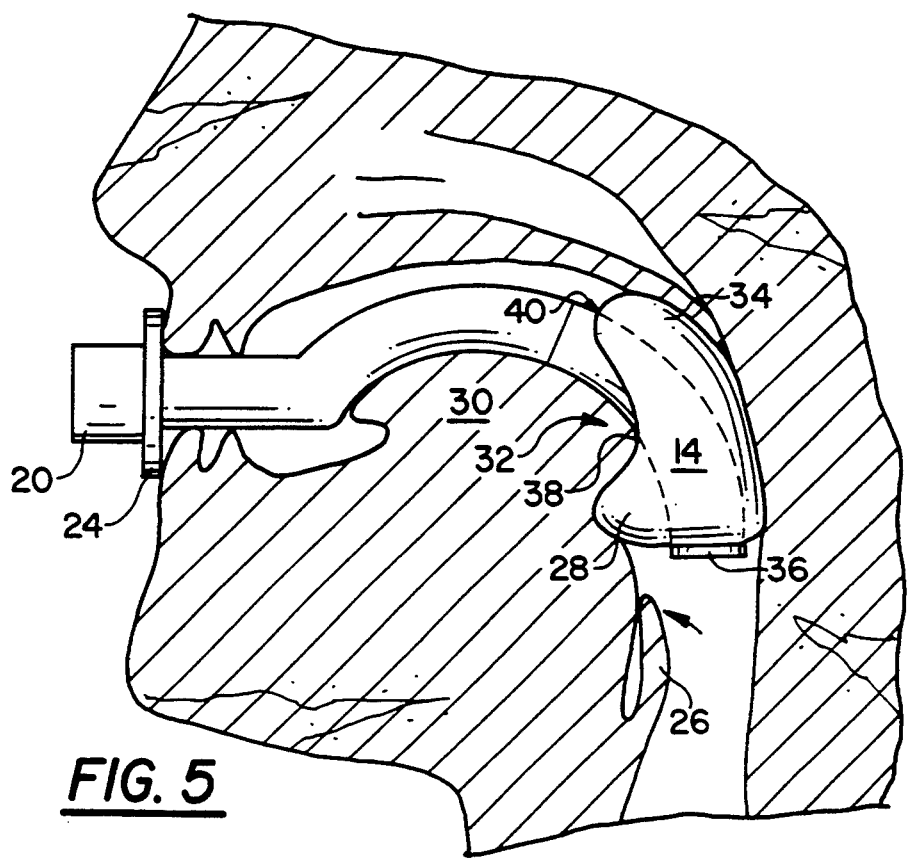
FIG. 5 is an elevational view showing a cuffed oro-pharyngeal airway in accordance with the invention disposed within a patient's oral cavity and with the cuff inflated.

As can be seen in FIGS. 4 and 5, the distal most tip 36 of the airway terminates proximal to the range of displacement of the epiglottis 26 so as not to interfere with the full range of motion of the epiglottis 26. As noted above, the inventive airway with cuff deflated performs like conventional airways. However, when the cuff is inflated, the protuberance 28 locks in behind the tongue 30 at the base of the tongue above the epiglottis 26.

As noted above, the cuff of the invention is characterized as being a high volume low pressure cuff. Thus the cuff will conform to differences in individual airways and will effectively seal the upper airway without generating pressures which might be likely to cause necrosis in the tissues it contacts. The anterior projecting portion 28 of the cuff displaces the epiglottis 26 anteriorly which opens the airway. Meanwhile the posterior portion 34 of the cuff engages and displaces the posterior portion of the soft palate against the nasopharynx thereby closing off the nasal passages from the oral cavity.

The device or COPA 10 is used initially as an ordinary oral airway. Thus, it is inserted into the patient's oro-pharynx after the patient is under general anesthesia. With the cuff deflated, the COPA establishes an airway column down the core of the device. Conventional face-mask/oral airway anesthesia can be maintained with the device in this fashion. With inflation of the cuff, the oro-pharynx is sealed circumferentially around the outside of the distal portion of the COPA. Attachment of the anesthesia circuit with the cuff inflated allows a sealed circuit to be established between the patient and the anesthesia machine. This prevents dangerous vapors from escaping into the atmosphere, allows for the monitoring of respiratory volumes, inspired and expired gas concentrations, and allows for gentle positive pressure ventilation. The inflation of the cuff will also distend the upper pharyngeal structures and open further the pharyngeal airway column. Once the cuff is inflated, the device will become stabilized in the patient's pharynx. For added stability, as mentioned above, a strap may be attached from behind the patient's neck to tabs or apertures on the tooth/lip guard.

The anterior displacement of the supra-laryngeal structures in accordance with the invention is a unique and advantageous feature thereof. More particularly, it is the ventral/anterior aspect of the cuff, which is substantially shorter than the posterior portion, that provides a locking feature in accordance with the invention. The anterior segment also displaces the supra-laryngeal structures including the base of the tongue, to help lift the epiglottis and hence aid in the establishment of a patent airway. The posterior aspect of the cuff aids in posteriorly displacing the soft palate to seal the nasal pharynx. The posterior portion of the cuff also aids in centrally positioning the core of the airway thereby properly directing air flow through the oral cavity and also provides a soft cushion to minimize pressure trauma to the posterior pharyngeal wall.

Ten patients were evaluated with the device in place during emergence from a short general anesthetic. In this small group, although there was no statistical difference between positive inspiratory pressure necessary to generate adequate ventilation volumes before (face-mask only) placement of the device, during placement with the cuff deflated, or with the cuff inflated, positive inspiratory pressure necessary to generate adequate ventilation volumes with the cuff inflated did tend to be less. Use of the device did not affect end-tidal carbon dioxide concentrations. No patient had a complication as a result of participating in this study. Thus, this new airway device, the COPA, is a feasible design for maintaining an airway during the administration of general anesthesia.

This study demonstrates that the use of a newly designed cuffed oropharyngeal airway may be used to support the airway with either gentle positive pressure or spontaneous breathing in patients undergoing general anesthesia for short procedures. This study also suggests that this new airway device, the cuffed oropharyngeal airway (COPA), is a feasible design for maintaining an airway during the administration of general anesthesia. This device thus has the potential to be a significant asset to the anesthesiologist.

Much of the impetus to design and evaluate this device was generated from the difficulties associated with short general anesthetics in children for ophthalmological examinations. It soon became apparent that this device might have many other potential uses including any procedure for which ordinary face mask/oral airway anesthesia might be suitable. Thus the inventive device may also be of value in more varied clinical situations.

Several design points make this device particularly interesting. First, it is based upon and strongly resembles the common oral airway. It may be used as an oral airway or bite block when the cuff is deflated. This makes it potentially more likely to be incorporated into the anesthesiologist's equipment list who might be weary of new, strange looking devices. Second, the placement of the cuff, when inflated, anteriorly displaces the pharyngeal structures as in the triple airway maneuver as described by Boidin and thereby lifts the epiglottis and keeps the airway patent. Although this does not protect the airway from aspiration of refluxed materials, the further opening of the pharyngeal structures may make positive pressure ventilation with lower pressures more effective and less likely to fill the stomach with air. Third, it allows the anesthesiologist to maintain an effective airway as in face mask/oral airway technique without constant hands-on commitment. This makes the administration of intravenous medications, adjustments for patient positioning, managing of the record, etc., easier. Finally, this device allows a simple and smooth transition from mask induction to spontaneously breathing general anesthesia with minimal obstructive devices in the area of the patient's face.

There are also several advantages the COPA offers over the laryngeal mask airway. First, in situations where one does not want to instrument, or even touch the laryngeal structures, including the epiglottis (as in fiberoptic evaluation of the airway during spontaneous breathing) the COPA may be used. The laryngeal mask airway, on the other hand is designed to come over the laryngeal structure and may thus distort their shape. Second, the COPA seems to be even simpler to use than the laryngeal mask airway and the basic structure is certainly more familiar to some anesthesiologists. Third, whereas the laryngeal mask airway has the potential to be obstructed by biting (unless an additional bite block is applied), the COPA's structure preferably incorporates such protection. Finally, because of the semi-rigid material of the COPA, it is not subject to the possibility of kinking.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A pharyngeal tube for insertion into the pharynx, comprising:
    a cannula having a first, distal end for placement within the pharynx of a patient, and a second, proximal end adapted to be disposed outside of the patient's oral cavity, said cannula having a length such that when the distal end is placed within the pharynx, it terminates distally at a point above the patient's epiglottis;
    an inflatable cuff means for forming a seal between a wall of said cannula and a wall of the patient's pharynx, said cuff means comprising a membrane mounted to said cannula wall so as to be disposed adjacent said distal end; and
    wherein said inflatable cuff means defines, on inflation, a ventral/anterior portion and a posterior portion, said ventral/anterior portion comprising a protuberance having a length along the side of the cannula facing said ventral/anterior portion less than or equal to approximately one half the length of the cannula which is covered by said posterior portion of the inflatable cuff means.

2. A pharyngeal tube as in claim 1, wherein said ventral/anterior portion is disposed on said cannula so as to displace, on inflation, a base of the patient's tongue, thereby locking said cannula in the pharynx and displacing the patient's epiglottis to an open disposition for anesthesia gas delivery to the lungs.

3. A pharyngeal tube as in claim 1, wherein said posterior portion is disposed on said cannula so as to displace, on inflation, the patient's soft palate against the nasopharynx to seal-off the nasal passage.

4. A pharyngeal tube as in claim 1, wherein said cuff means is collapsible so that on deflation it can be disposed substantially flush against the wall of the cannula for insertion of said cannula into the pharynx.

5. A pharyngeal tube as in claim 1, wherein said cuff means is formed from a substantially inelastic material and is collapsed against said wall by evacuating an inflation medium therefrom.

6. A pharyngeal tube as in claim 1, further comprising a tooth/lip guard on said cannula adjacent said proximal end.

7. A pharyngeal tube as in claim 6, wherein said tooth/lip guard includes a flange element which projects in a plane that intersects a central axis of the cannula so as to be inclined with respect thereto.

8. A pharyngeal tube as in claim 6, wherein said tooth/lip guard includes a flange element which projects in a plane that intersects a central axis of the cannula at an angle of about 90 degrees.

9. A pharyngeal tube as in claim 1, wherein said cannula has a proximal straight portion, an upwardly arched intermediate portion and a downwardly depending distal portion and is formed from a semi-rigid material that resists kinking.

10. A device as in claim 1, including means for locking the cannula in place within the patient's oropharynx, said means for locking comprising a portion of said cuff means which defines, on inflation, a ventral/anterior portion, said ventral/anterior portion comprising a protuberance having a length substantially less than a length of a posterior portion of said cuff means.

11. An oral airway for administering anesthesia gases to a patient, comprising:
    an elongated tubular member having a distal end and a proximal end and a central axis, said tubular member having a length such that said proximal end is adapted to be disposed adjacent to but outside the oral cavity of the patient and the distal end is adapted to be disposed in the lower pharynx of the patient, above the epiglottis;
    an inelastic, inflatable member mounted to said tubular member adjacent said distal end, said inflatable member, on inflation, displacing the soft palate against the nasopharynx to seal-off the nasal passage and defining a seal between an outer wall of said tubular member and the pharyngeal wall, said inflatable member further displacing a base of the patient's tongue, thereby locking said tubular member in the pharynx and displacing the patient's epiglottis to an open disposition for anesthesia gas delivery to the lungs; and
    means for conveying a pressure fluid between a source of pressurized fluid outside the patient's oral cavity and said inflatable member, for selective inflation and deflation thereof, said inflatable member defining, on inflation, a ventral/anterior portion and a posterior portion, said ventral/anterior portion including a protuberance which has a length less than or equal to approximately one half of a length of said posterior portion.

12. An oral airway as in claim 11, wherein said ventral/anterior portion is constructed and arranged to displace the base of the patient's tongue, and the posterior portion is constructed and arranged to displace the patient's soft palate.

13. An oral airway as in claim 11, wherein said inflatable member is collapsible against the wall of the cannula for insertion of said tubular member into the pharynx, and wherein said inflatable member comprises a membrane secured to the wall of the cannula so that the wall of the cannula is a wall of the inflatable member.

14. An oral airway as in claim 11, further comprising a tooth/lip guard provided on said cannula adjacent said proximal end.

15. An oral airway as in claim 11, wherein said cannula has an upwardly arched intermediate portion and a downwardly depending distal portion.

16. An oral airway as in claim 11, wherein said cannula has a proximal straight portion, an upwardly arched intermediate portion and a downwardly depending distal portion.

17. A method of administering anesthesia to a patient, comprising the steps of:
providing a device comprising a cannula having a first, distal end for placement within the pharynx of a patient, a second, proximal end adapted to be disposed outside of the patient's oral cavity, and a flow passage therebetween, said cannula having a length such that when the distal end is placed within the pharynx, it terminates distally at a point above the patient's epiglottis; and an inflatable cuff means for forming a seal between a wall of said cannula and a wall of the patient's pharynx, said cuff means comprising a membrane mounted to said cannula wall so as to be disposed adjacent said distal end, said cuff means having, on inflation, first inflated portion along one side that is less than or equal to approximately one half of a length of a second inflated portion on the diametrically opposite side of said cannula;
inserting said device, with cuff deflated, into a patient's oro-pharynx so that said distal end of said device is disposed at a point above the patient's epiglottis thereby to establish an airway column down the core of the device;
inflating said cuff means to seal the oro-pharynx, distend the upper pharyngeal structures to open further the pharyngeal airway column, and lock the cannula in place in the pharynx; and
attaching an anesthesia circuit to said proximal end of said cannula.

18. A method as in claim 17, wherein said step of providing comprises providing a device including a tooth/lip guard having means for attaching a stabilizing strap thereto and further comprising attaching a strap to the tooth/lip guard.

19. A method as in claim 17, wherein said step of providing comprises providing a device having a cuff means comprising a membrane sealed to the wall of the cannula so that an inflatable compartment of said cuff means is bounded by said membrane and said wall.

20. A method as in claim 17, wherein said step of providing comprises providing a device having an inflatable cuff means that defines, on inflation, a ventral-/anterior portion and a posterior portion, said ventral-/anterior portion comprising the shorter of two lengths and said step of inflating includes inflating the cuff means to displace a base of the patient's tongue with the protuberance, thereby locking said cannula in the pharynx and displacing the patient's epiglottis to an open disposition for anesthesia gas delivery to the lungs.

* * * * *